United States Patent
Bauer et al.

[11]
[45] Apr. 21, 1981

[54] 3-METHYL-ALDEHYDES, PROCESSES FOR THEIR PREPARATION AND THEIR USE AS ODORANTS

[75] Inventors: Kurt Bauer, Holzminden; Detlef Hagena, Hoexter; Hans-Otto Müller, Holzminden, all of Fed. Rep. of Germany

[73] Assignee: Haarmann & Reimer GmbH, Holzminden, Fed. Rep. of Germany

[21] Appl. No.: 71,349

[22] Filed: Aug. 30, 1979

[30] Foreign Application Priority Data

Jul. 20, 1979 [DE] Fed. Rep. of Germany ....... 2929340

[51] Int. Cl.³ ............................................. C07C 47/02
[52] U.S. Cl. ................................. 260/601 R; 568/448
[58] Field of Search .................................... 568/448

[56] References Cited
PUBLICATIONS

Manni et al., Chem. Abstract, vol. 74, (1971), p. 69301u.
Brown et al., J. Amer. Chem. Society, vol. 92/3, Feb. 11, 1970 pp. 714–716.
Djerassi et al., J. Amer. Chem. Society, vol. 81, Jun. 5, 1959, pp. 2789–2794.

*Primary Examiner*—Werren B. Lone
*Attorney, Agent, or Firm*—Sprung, Felfe, Horn, Lynch & Kramer

[57] ABSTRACT

The invention concerns new 3-methyl-aldehydes of the general formula

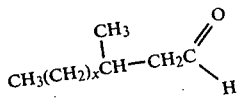

wherein
x is 6 or 7,
a process for their preparation and their use as odorants.

1 Claim, No Drawings

3-METHYL-ALDEHYDES, PROCESSES FOR THEIR PREPARATION AND THEIR USE AS ODORANTS

The invention relates to 3-methylaldehydes of the formula:

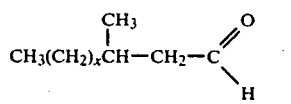

in which
x represents 6 or 7.

The invention further relates to processes for the preparation of the 3-methylaldehydes of the formula (I). The processes are characterised in that either an acid of the formula:

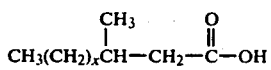

in which
x has the meaning mentioned under formula I is reduced according to methods known for the reduction of carboxylic acids to form aldehydes, or an alcohol of the formula:

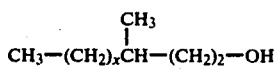

in which
x has the meaning mentioned under formula I is oxidised according to methods known for the oxidation of alcohols to form aldehydes.

In addition the invention relates to the use of the 3-methylaldehydes of formula (I) as odorants.

The reduction of the acids may be conducted in the gas phase using a manganese-(II)-oxide catalyst. To achieve this the acid and a 2 to 6 times', preferably 4 to 5 times', excess of formic acid are evaporated separately in vacuo and at a reaction temperature of 340° to 400° C., preferably 360° C., are passed over a manganese-(II)-oxide pumice catalyst.

A further possibility is the reduction method according to Rosenmund. In this the acids are converted into their acid chloride using thionyl chloride, phosphorus trichloride or phosphorus pentachloride and the acid chloride is reduced to the aldehyde using hydrogen and an inactivated palladium catalyst. The palladium catalyst, 5% palladium on a carrier such as kieselguhr, calcium carbonate, activated charcoal, but preferably barium sulphate, is used in an amount of 5% to 10% by weight, based on the acid chloride. The inactivation is conducted by the addition of quinoline sulphur, thiourea or phenyl isothiocyanate. When using thionyl chloride for the preparation of the acid chloride the inactivation may be omitted since the impurities remaining in the acid chloride are sufficient to deactivate the catalyst. The reduction is conducted in an inert solvent such as xylene, toluene or tetralin at temperatures between 100° and 180° C.

The oxidation of the alcohols of the formula (III) to form the aldehydes of the formula (I) can be conducted with chromic acid in sulphuric acid. However, catalytic dehydrogenation in which copper, silver, or zinc compounds, preferably copper chromium oxide, are used as catalyst, has been found to be advantageous. The reaction may be conducted in the form of a liquid phase dehydrogenation at the boiling point of the alcohol using 10% by weight of catalyst or in the form of a vapour phase dehydrogenation at 400° to 700° C. using a solid contact.

The preparation of the acids of the formula (II) may be conducted according to the following method: Hexanoic or heptanoic acid chloride are reacted with dimethylacrylic acid ethyl ester in the presence of a Friedel Craft catalyst to form a 3-methyl-5-oxo-alkanoic acid ethyl ester unsaturated in one position. From this ester the acids of formula (II) are produced by hydrogenation in the presence of Raney nickel and subsequent reduction with hydrazine according to the Wolff-Kishner method.

The alcohols of formula (III) may be obtained from the acids of formula (II) by reduction using lithium aluminium hydride. It has been found to be advantageous to first of all convert the acids into the ethyl esters, in order to then reduce the latter with lithium aluminium hydride or to hydrogenate them in an autoclave using hydrogen and a copper chromium oxide catalyst.

The 3-methylaldehydes according to the invention are valuable odorants, which are of a citrus-like waxy nature and which may be described as being radiant, powerful, clinging and harmonious and which are particularly suitable for the formation of odorant complexes together with other components.

Furthermore 3-methyldecanal has a cyclamen-like ozonic green note as is found in the skin of South-American limes, whereas 3-methylundecanal embodies very well the top note of the mandarine skin.

The 3-methylaldehydes according to the invention are superior to the isomeric 2-methylaldehydes already known as odorants in that they possess new odorant notes and a scent which is finer and more rounded off in itself.

The compounds according to the invention are used in mixtures with other odorants in odorant compositions, e.g. in amounts of from 0.01% to 20% by weight, preferably in amounts of from approximately 0.1% to 10% by weight, based on the total weight.

The field of application of the compounds according to the invention is extraordinarily wide owing to their harmonious type of scent and their advantageous use properties, e.g. their stability in aggressive media. They are suitable for use in perfume compositions for the most varied finished products, e.g. for high-quality cosmetics, for fine perfumery articles such as extracts, soaps, deodorant sprays, shampoos, foam baths and for detergents.

EXAMPLE 1

546.6 g (3.17 mols) 3-methyl-decanol are heated with 54.6 g copper chromium oxide to boiling temperature. 428 g of destillate are formed under generation of hydrogen. From this, by means of fine distillation 156.2 g 3-methyl-decanol are recovered. 244.4 g 3-methyl-decanol having a boiling point of 46° C./0.1 mm Hg are obtained, corresponding to a yield of 63.4% of theory, based on the converted alcohol.

The 3-methyl-decanol used as starting material is prepared according to the following method:

700 g (5.2 mols) hexanoic acid chloride and 666 g (5.2 mols) dimethylacrylic acid ethyl ester are simultaneously introduced at 30° C. over a period of 3 hours to a suspension of 1533 g (11.48 mols) aluminium chloride in 850 ml methylene chloride. When the addition is completed the reaction mixture is heated for 3 hours to reflux temperature and then hydrolysed with ice water. The aqueous phase is extracted twice, each time with 150 ml methylene chloride, the combined organic phases are washed until neutral and the solvent is drawn off. 1130 g of crude 3-methyl-5-keto-2(3)-decenoic acid ethyl ester (b.p.$_{0.3}$:93° C.) are obtained corresponding to a yield of 96% of theory.

1130 g (5 mole) 3-methyl-5-keto-2(3)-decenoic acid ethyl ester are introduced with 336 g (6 mols) potassium hydroxide, 400 ml ethanol and 1300 ml water into an autoclave and hydrogenated at 40° C. and 40 atm. hydrogen pressure under the addition of 120 g Raney nickel. The hydrogen absorption is 87% of theory. After filtering off the catalyst the reaction solution is acidified with sulphuric acid and extracted with ethyl acetate. The ethyl acetate solution is separated off and freed from solvent. 915 g of crude 3-methyl-5-keto-decanoic acid remain.

This crude 3-methyl-5-keto-decanoic acid is heated, without being purified any further, with 473 ml diethylene glycol, 1260 g (22.5 mols) potassium hydroxide and 850 g (17 mols) 80% strength hydrazine hydrate for 2 hours to reflux temperature. Then water and excess hydrazine are distilled off and the reaction temperature is increased for 1 hour to 210° to 220° C. After cooling the reaction mixture is mixed with 400 ml toluene and 400 ml water, acidified with hydrochloric acid and poured on to a mixture of water and ice. The organic phase is separated off; the aqueous phase is extracted twice with toluene. The combined organic phases are washed until neutral and are freed from solvent. 707.8 g 3-methyldecanic acid (b.p.$_{0.8}$:110° C.), corresponding to a yield of 76.1% of theory, based on the 3-methyl-5-keto-2(3)-decenoic acid ethyl ester.

707.8 g (3.8 mols) 3-methyl-decanoic acid are heated in 305.9 g ethanol and 700 ml toluene, which is mixed with 19 g p-toluenesulphonic acid, for 6 hours with refluxing using a water separator. Following the working-up process 740.5 g 3-methyl-decanoic acid ethyl ester (b.p.$_{0.5}$:75° C.) are obtained, corresponding to a yield of 91% of theory.

740 g (3.46 mols) 3-methyl-decanoic acid ethyl ester, dissolved in 600 ml ether, are added while cooling to a suspension of 72 g (1.89 mols) lithium aluminium hydride in 600 ml ether. After the addition has ended the reaction mixture is heated for one hour to reflux temperature, is then hydrolysed and acidified with sulphuric acid. The organic phase is separated off, the aqueous phase is extracted with ether and the combined organic phases are freed from solvent. The destillation of the residue gives 529.5 g 3-methyldecanol (b.p.$_{0.3}$:83° C.), corresponding to a yield of 88.9% of theory.

EXAMPLE 2

286.8 g (1.54 mols) 3-methyl-undecanol are, in the same way as in Example 1, subjected to liquid phase dehydrogenation with 28.7 g copper chromium oxide. 126.6 g 3-methyl-undecanol having a boiling point of 56° C./0.2 mm Hg, are obtained, corresponding to a yield of 64.5% of theory, based on the reacted alcohol.

The starting compound 3-methyl-undecanol (b.p.$_{0.5}$:105° C.) is prepared, in the same way as that described in Example 1 for the preparation of 3-methyl-decanol, from hexanoic acid chloride and dimethylacrylic acid ethyl ester.

EXAMPLE 3

A perfume composition with a citrus note is prepared by mixing the following components: 200 lemon oil terpene; 30 citral; 20 citrathal PPL; 5 geranitrile; 3 tagetes oil; 2 trimethyltetrahydrobenzaldehyde; 5 trimethylundecylene aldehyde; 50 petit-grain oil Paraguay; 100 menthanyl acetate; 250 terpineol; 10 coriander oil; 5 rosemary oil; 20 galbanum resinoid; 50 dihydro-nor-dicyclo-pentadienylacetate; 20 styrolyl acetate; 5 eugenol; 50 α-hexylcinnamaldehyde; 5 2-n-heptyl-cyclopentanone-1; 10 p-tert.-butyl-α-methyl-hydrocinnamaldehyde; 30 benzylsalicylate; 10 pentadecanolide, 50% strength in triethyl citrate; 70 diethyl phthalate; 30 phenoxyethylisobutyrate: total 1,000 parts by weight.

By adding 20 parts by weight 3-methyldecanal the composition is given a vivacious freshness, fullness and harmony.

EXAMPLE 4

A perfume composition with an exotic note is prepared by mixing the following components: 100 bergamot oil Reggio; 50 orange oil Florida; 10 clove bud oil; 40 eugenol; 30 geranyl acetate; 5 galbanum resinoid; 3 oil of bay; 2 cinnamon bark oil; 1 cistus oil; 10 Peru balsam oil; 10 cinnamyl alcohol ex Storax; 70 β-phenylethylalcohol; 10 rose abs. de Mai; 5 hyacinthe abs.; 20 ylang-ylang oil; 5 jasmin abs.; 10 methyldihydrojasmonate; 1 undecalactone; 50 hydroxycitronellal; 20 p-tert-butyl-α-methylcinnamaldehyde; 5 styrolylacetate; 1 allyl ionone; 30 γ-methyl ionone; 10 heliotropin; 100 benzyl salicylate; 30 sandalwood Mysore (East-Indian); 50 acetyl cedrene; 30 patchouli oil Singapore; 20 vetiveryl acetate; 5 oak moss abs. 50% strength in triethyl citrate; 1 civet; 20 coumarin; 3 ethyl-vanillin; 20 musk Ketone; 213 diethyl phthalate: total 990 parts by weight.

By adding 10 parts by weight of 3-methylundecanal the composition is given elegance, radiant power and the characteristic freshness desired of exotic perfume.

What is claimed is:

1. 3-methyl-aldehydes of the general formula:

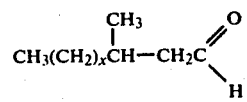

wherein
x is 6 or 7.

* * * * *

UNITED STATES PATENT AND TRADEMARK OFFICE
CERTIFICATE OF CORRECTION

PATENT NO. : 4,263,459
DATED : April 21, 1981
INVENTOR(S) : Kurt Bauer et al

It is certified that error appears in the above—identified patent and that said Letters Patent is hereby corrected as shown below:

Column 3, line 38, "3-methyldecanic" should be "3-methyldecanoic".

Column 4, line 8, "hexanoic" should be "heptanoic".

Signed and Sealed this

Twenty-second Day of September 1981

[SEAL]

Attest:

Attesting Officer

GERALD J. MOSSINGHOFF
Commissioner of Patents and Trademarks